(12) United States Patent
Liu et al.

(10) Patent No.: US 12,410,230 B2
(45) Date of Patent: Sep. 9, 2025

(54) ANTI-ANGIOGENIC AGENT AND METHODS OF USING SUCH AGENT

(71) Applicant: Georgia State University Research Foundation, Atlanta, GA (US)

(72) Inventors: Zhi-Ren Liu, Marietta, GA (US); Jenny Yang, Marietta, GA (US)

(73) Assignee: Georgia State University Research Foundation

( * ) Notice: Subject to any disclaimer, the term of this patent is extended or adjusted under 35 U.S.C. 154(b) by 191 days.

(21) Appl. No.: 18/169,097

(22) Filed: Feb. 14, 2023

(65) Prior Publication Data
US 2024/0034766 A1 Feb. 1, 2024

Related U.S. Application Data

(63) Continuation-in-part of application No. 14/928,890, filed on Oct. 30, 2015, now Pat. No. 11,578,114, which is a continuation of application No. 13/739,241, filed as application No. PCT/US2011/043907 on Jul. 13, 2011, now Pat. No. 9,175,063.

(60) Provisional application No. 61/363,933, filed on Jul. 13, 2010.

(51) Int. Cl.
 C07K 14/705 (2006.01)
 A61K 38/17 (2006.01)
 A61K 45/06 (2006.01)

(52) U.S. Cl.
 CPC .... C07K 14/70507 (2013.01); A61K 38/1774 (2013.01); A61K 45/06 (2013.01)

(58) Field of Classification Search
 CPC .......... C07K 14/70507; A61K 38/1774; A61K 45/06
 See application file for complete search history.

(56) References Cited

U.S. PATENT DOCUMENTS

2004/0136987 A1* 7/2004 Wallner ............. C07K 16/2824
 424/144.1

* cited by examiner

Primary Examiner — Li N Komatsu
(74) Attorney, Agent, or Firm — Smith, Gambrell & Russell, LLP; Judy Jarecki-Black; Sharon Ngwenya

(57) ABSTRACT

Anti-angiogenic agents or polypeptides have an amino acid segment substantially similar to domain one of CD2. The polypeptide has a β-sheet formed by two segments. Methods of using such agents and polypeptide are also included.

17 Claims, 15 Drawing Sheets

Specification includes a Sequence Listing.

M4A4 = epithelial

M1WT = Angio1   CD2 = host   HUVEC = endothelial

In vitro activity for the viability of endothelial HUVEC cells

| | EC*$_{50}$ (μM) |
|---|---|
| Angio1 | 1.47 +/- 0.3 |
| Angio3 | 0.94 +/- 0.4 |
| Angio5 | 2.03 +/- 0.4 |

*EC$_{50}$ is defined as at the concentration point where Cell viability is 50% of buffer treated cells

Proteins expressed in bacterial E.coli

^Proteins expressed in yeast Pichia. Protein is glycosylated

FIG. 13

ANTI-ANGIOGENIC AGENT AND METHODS OF USING SUCH AGENT

PRIOR RELATED APPLICATION DATA

This application is a continuation-in-part of U.S. patent application Ser. No. 14/928,890, filed Oct. 15, 2015, now U.S. Pat. No. 11,578,114, which is a continuation of U.S. patent application Ser. No. 13/739,241, now U.S. Pat. No. 9,175,063, which is a U.S. National Phase of International Patent Application No. PCT/2011/043907, filed on Jul. 13, 2011, which claims the benefit of priority of U.S. Provisional Patent Application Ser. No. 61/363,933, filed Jul. 13, 2010, which are all incorporated by reference.

GOVERNMENT LICENSE RIGHTS

This invention was made with U.S. Government support under Grant No. CA118113 awarded by the National Institutes of Health. The U.S. Government has certain rights in the invention.

INCORPORATION BY REFERENCE OF SEQUENCE LISTING

The Sequence Listing titled 065480.010US3.xml which was created on May 8, 2025 and is 12,627 bytes in size, is hereby incorporated by reference in its entirety.

TECHNICAL FIELD

This disclosure relates to the inhibition or prevention of angiogenesis to control or treat an angiogenic dependent condition, a condition characterized by, or dependent upon, blood vessel proliferation. The disclosure further relates to the use of an anti-angiogenic agent in combination with a chemotherapeutic agent.

BACKGROUND

Angiogenesis is the process by which new blood vessels are formed from extant capillaries, while vasculogenesis involves the growth of vessels deriving from endothelial progenitor cells. Angiogenesis is a combinatorial process that is regulated by a balance between pro- and anti-angiogenic molecules. Angiogenic stimuli (e.g. hypoxia or inflammatory cytokines) result in the induced expression and release of angiogenic growth factors such as vascular endothelial growth factor (VEGF) or fibroblast growth factor (FGF). These growth factors stimulate endothelial cells (EC) in the existing vasculature to proliferate and migrate through the tissue to form new endothelialized channels. Angiogenesis is involved in the proliferation of endothelial cells.

Inappropriate, or pathological, angiogenesis is involved in the growth of atherosclerotic plaque, diabetic retinopathy, degenerative maculopathy, retrolental fibroplasia, idiopathic pulmonary fibrosis, acute adult respiratory distress syndrome, and asthma. Furthermore, tumor progression is associated with neovascularization, which provides a mechanism by which nutrients are delivered to the progressively growing tumor tissue. While the concept of slowing or even halting the progression of cancer by targeting its blood supply was first proposed more than 30 years ago, angiogenesis inhibitors are only now entering the mainstream of cancer therapeutics.

Accordingly, there is always a need in the art for methods and agents of reducing pathological angiogenesis. It is to this need, among others, that this disclosure is directed.

BRIEF DESCRIPTION OF THE FIGURES

FIG. 13 shows a graphic representation of the viability of various examples of the anti-angiogenic agent.

DEFINITIONS

Figure 1A:
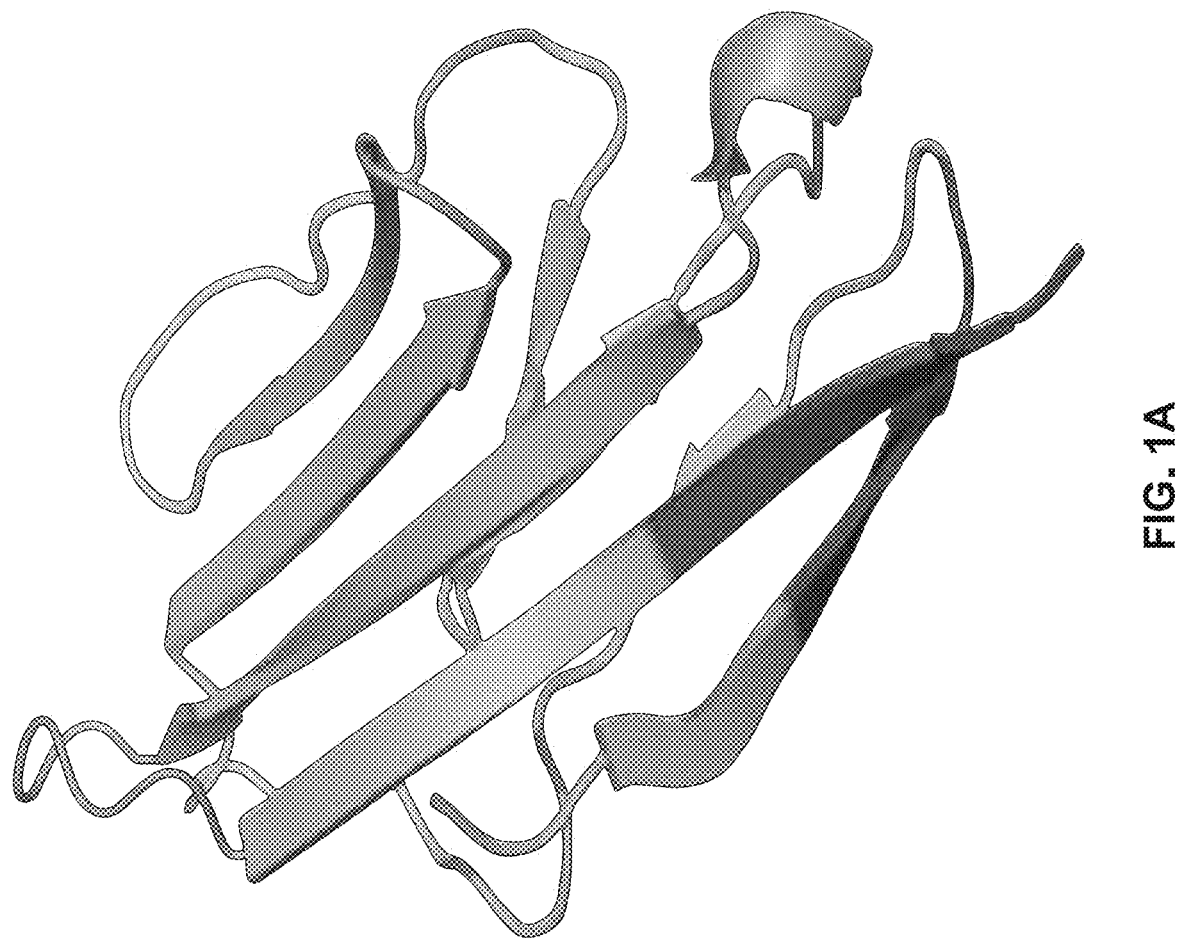
FIG. 1A is a schematic drawing of an anti-angiogenic agent showing the two short strands of the anti-parallel β-sheet of the protein.

The following definitions are provided to facilitate understanding of certain terms used throughout this specification.

"Angiogenesis" is defined as any alteration of an existing vascular bed or the formation of new vasculature which benefits tissue perfusion. This includes the formation of new vessels by sprouting of endothelial cells from existing blood vessels or the remodeling of existing vessels to alter size, maturity direction or flow properties to improve blood perfusion of tissue.

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to compounds that have the same basic chemical structure as a naturally occurring amino acid, by way of example only, an alpha-carbon that is bound to a hydrogen, a carboxyl group, an amino group, and an R group. Such analogs may have modified R groups (by way of example, norleucine) or may have modified peptide backbones, while still retaining the same basic chemical structure as a naturally occurring amino acid. Non-limiting examples of amino acid analogs include homoserine, norleucine, methionine sulfoxide, methionine methyl sulfonium.

The term "conservatively modified variants" applies to both natural and non-natural amino acid and natural and non-natural nucleic acid sequences, and combinations thereof. With respect to particular nucleic acid sequences, "conservatively modified variants" refers to those natural and non-natural nucleic acids which encode identical or essentially identical natural and non-natural amino acid sequences, or where the natural and non-natural nucleic acid does not encode a natural and non-natural amino acid sequence, to essentially identical sequences. By way of example, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Thus by way of example every natural or non-natural nucleic acid sequence herein which encodes a natural or non-natural polypeptide also describes every possible silent variation of the natural or non-natural nucleic acid. One of skill will recognize that each codon in a natural or non-natural nucleic acid (except AUG, which is ordinarily the only codon for methionine, and TGG, which is ordinarily the only codon for tryptophan) can be modified to yield a functionally identical molecule. Accordingly, each silent variation of a natural and non-natural nucleic acid which encodes a natural and non-natural polypeptide is implicit in each described sequence.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. By way of example, an agent or a compound being administered includes, but is not limited to, a natural amino acid polypeptide, non-natural amino acid polypeptide, modified natural amino acid polypeptide, or modified non-amino acid polypeptide. Compositions containing such natural amino acid polypeptides, non-natural amino acid polypeptides, modified natural amino acid polypeptides, or modified non-natural amino acid polypeptides can be administered for prophylactic, enhancing, and/or therapeutic treatments. An appropriate "effective" amount in any individual case may be determined using techniques, such as a dose escalation study.

The term "nucleic acid sequence" as used herein, refers to the order and identity of the nucleotides comprising a nucleic acid.

The term "Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants" as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "pharmaceutically acceptable", as used herein, refers to a material, including but not limited, to a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "prophylactically effective amount," as used herein, refers that amount of a composition containing at least one non-natural amino acid polypeptide or at least one modified non-natural amino acid polypeptide prophylactically applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The phrase "substantially similar," in the context of two nucleic acids or polypeptides, refers to two or more sequences or subsequences that have at least 75%, preferably at least 85%, more preferably at least 90%, 95% or higher or any integral value therebetween nucleotide or amino acid residue identity, when compared and aligned for maximum correspondence, as measured using a sequence comparison algorithm such as those described below for example, or by visual inspection. Preferably, the substantial identity exists over a region of the sequences that is at least about 10, preferably about 20, more preferable about 40-60 residues in length or any integral value therebetween, preferably over a longer region than 60-80 residues, more preferably at least about 90-100 residues, and most preferably the sequences are substantially identical over the full length of the sequences being compared, such as the coding region of a nucleotide sequence for example.

The term "synergistic", as used herein, refers to a combination of prophylactic or therapeutic effective agents which is more effective than the additive effects of any two or more single agents. A synergistic effect of a combination of prophylactic or therapeutic agents may permit the use of lower dosages of one or more of the agents and/or less frequent administration of the agents to a subject with a specific disease or condition. In some cases, a synergistic effect of a combination of prophylactic or therapeutic agents may be used to avoid or reduce adverse or unwanted side effects associated with the use of any single therapy.

The term "therapeutically effective amount," as used herein, refers to the amount of a composition containing at least one non-natural amino acid polypeptide and/or at least one modified non-natural amino acid polypeptide administered to a patient already suffering from a disease, condition or disorder, sufficient to cure or at least partially arrest, or relieve to some extent one or more of the symptoms of the disease, disorder or condition being treated. The effectiveness of such compositions depend on conditions including, but not limited to, the severity and course of the disease, disorder or condition, previous therapy, the patient's health status and response to the drugs, and the judgment of the treating physician. By way of example only, therapeutically effective amounts may be determined by routine experimentation, including but not limited to a dose escalation clinical trial.

DETAILED DESCRIPTION

This disclosure provides an anti-angiogenic agent and a method of inhibiting angiogenesis in which the dependent condition in a mammal is treated by administering an anti-angiogenic agent to the mammal, in a therapeutically effective amount and frequency to produce a regression or arrest of the condition without significant toxicity. The angiogenic dependent condition may be selected from the group consisting of neoplasm, including a solid tumor neoplasm, including breast carcinoma, lung carcinoma, prostate carcinoma, colon carcinoma, prostate carcinoma, ovarian carcinoma, neuroblastoma, central nervous system tumor, neuroblastoma, glioblastoma multiforme or melanoma. While no list can be complete, the anti-angiogenic agent may be used to produce a regression or arrest of most, if not all, solid tumors. The mammal receiving the treatment can be a human.

Figure 1C:
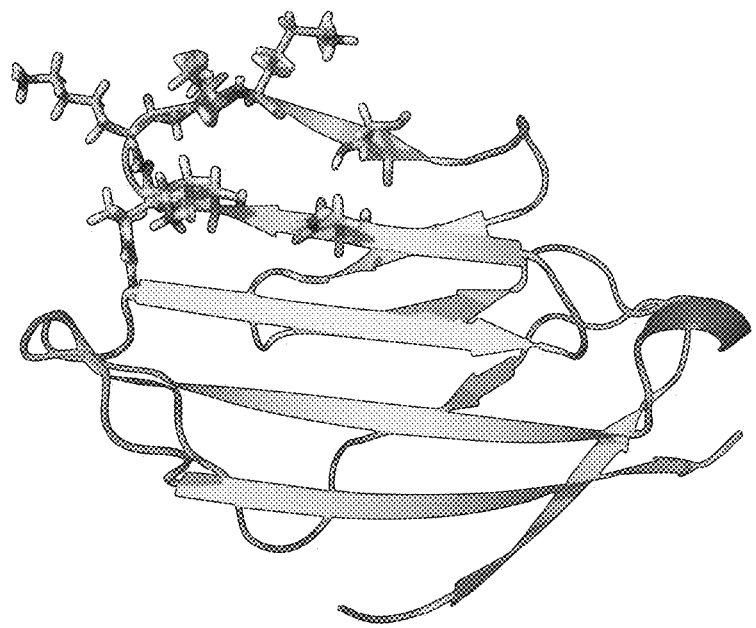
FIG. 1C is another schematic drawing of an anti-angiogenic agent showing the two short strands of the anti-parallel β-sheet of the protein in which the hydrophobic surface is facing inward.
Figure 1B:
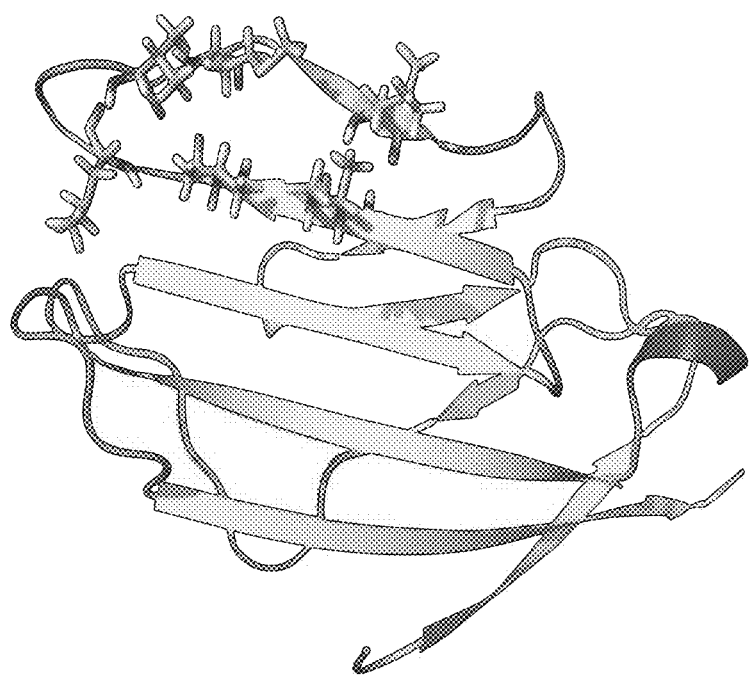
FIG. 1B is another schematic drawing of an anti-angiogenic agent showing the two short strands of the anti-parallel β-sheet of the protein in which the hydrophobic surface is facing outward.

In one specific embodiment, the anti-angiogenic agent includes a variation of polypeptides derived from domain one of CD2, which may originate from human and non-human sources. More specifically, the structure and function of domain one of CD2 were altered to prepare new polypeptides with varied stability and activity. In some examples, the alterations could be used to prepare at least two short strands of anti-parallel β-sheets (e.g. FIGS. 1A, 1B, and 1C) that mimic the active moiety of several endogenous anti-angiogenic polypeptides, such as PF4, IL8, TSP-1, Endostatin, and other synthetic peptides. In some examples, the anti-angiogenic agent or polypeptide can have a β-sheet formed by two segments, an anti-parallel fold, an inward-facing hydrophobic surface, an outward-facing hydrophilic surface; and the two segments have at least four amino acids. In other examples, it was found that six or more amino acids constituted a segment. In yet other examples, it was found that eight or more amino acids constituted a segment. The amino acid residues may alternate between hydrophilicity and hydrophobicity (e.g., hydrophilic-hydrophobic-hydrophilic-hydrophobic or hydrophilic-hydrophobic-hydrophobic).

The anti-angiogenic agents have many in vivo, in vitro and ex vivo utilities, which include anti-angiogenic properties in clinical and non-clinical settings. Methods for preparing or creating systematic polypeptide variation through directed evolution techniques are known in the art. It is contemplated and understood that methods disclosed herein may be used to prepare other non-CD2 polypeptides with at least two short strands of an anti-parallel β-sheet.

In one embodiment, the anti-angiogenic agent can be prepared using rational polypeptide design. Rational design includes methods in which the amino acid residues in a polypeptide sequence are identified and predicted to have a specific impact on a polypeptide. For example, one such method includes preparing a training set of polypeptide variants in which the data provides activity and sequence information for each polypeptide variant in the training set; deriving an activity model that is able to predict the activity based on alterations of specific amino acid; and using the model to identify one or more amino acids at specific positions in one or more polypeptides that have specific activities and properties.

In another specific embodiment, the anti-angiogenic agent can be prepared by creating mutations within the host polypeptide or domain one of CD2 (e.g. SEQ ID NOS: 4, 5, and 7).

One of ordinary skill in the art can prepare specific anti-angiogenic agents using recombinant technology. For example, one may prepare the appropriate nucleic acid of the polypeptides or polypeptides in SEQ ID NOS: 1-11 using ordinary methods. Alternatively, the polypeptides of SEQ ID NOS: 1-11 can be generated by site directed mutagenesis techniques, to produce a desired anti-angiogenic agent. Any nucleic sequence which differs from any sequence, including SEQ ID NOS:1 through 11, may be altered due to the degeneracy of the genetic code. The mutated nucleic acid sequence may then be subcloned into an appropriate expression vector and expressed in a host such as yeast or *E. coli*. After preparation, purification techniques are obvious to those with ordinary skill in the art.

In one embodiment, the anti-angiogenic agent can include N-linked glycosylation. The N-linked glycosylation process occurs in eukaryotes and has implications in polypeptide folding, polypeptide solubility, and long blood circulation. N-linked glycosylation may require the consensus sequence Asn-X-Ser/Thr and occurs more often when this consensus sequence occurs in a loop in the peptide. In one example, i.e., in yeast *Pichia* expression system, the N-linked glycosylation sites were at positions N65.

In some specific embodiments, the anti-angiogenic agents control or inhibit angiogenesis. The inhibition of angiogenesis is generally considered to be the halting of the development of new blood vessels, whether they develop by sprouting or by the arrival and subsequent differentiation into endothelial cells of circulating stem cells. However, since the anti-angiogenic agent can induce apoptosis of activated endothelial cells, inhibition of angiogenesis should also be construed to include the killing of cells, particularly cells in existing vessels near or within a tumor when activated by tumor angiogenesis factors. Thus, within the context of the present invention, inhibition of angiogenesis should be construed to include inhibition of the development of new vessels, which inhibition may or may not be accompanied by the destruction of nearby existing vessels.

The anti-angiogenic agent appears to inhibit or prevent angiogenesis by inhibiting or controlling apoptosis. The developed polypeptides demonstrated strong activity in the induction of endothelial cell apoptosis without effects on epithelial and fibroblast cells in the in vitro analyses. In addition, the developed polypeptides exerted less effect on tube structure formed by HUVEC cells, which suggests less toxicity on already existing normal blood vessels. Survival factors include vascular endothelial cell growth factors or mitogens, as well as those factors which do not appear to have a direct growth-stimulatory effect but allow the cells to recover from injury.

These anti-angiogenic agents may be incorporated into methods of treating a mammal by inhibiting angiogenesis that include the steps of administering the anti-angiogenic agents. In certain embodiments, the anti-angiogenic polypeptide exhibited extended circulation time compared to small molecules and short peptide agents.

Specific embodiments provide methods of inhibiting angiogenesis and methods of treating angiogenesis-associated diseases. In other embodiments, the present invention provides methods of inhibiting or reducing tumor growth and methods of treating an individual suffering from cancer. These methods involve administering to the individual a therapeutically effective amount of one or more polypeptide therapeutic agents as described above. These methods are particularly aimed at therapeutic and prophylactic treatments of animals, and more particularly, humans.

As described herein, angiogenesis-associated diseases include, but are not limited to, angiogenesis-dependent cancer, including, for example, solid tumors, blood born tumors such as leukemias, and tumor metastases; benign tumors, for example hemangiomas, acoustic neuromas, neurofibromas, trachomas, and pyogenic granulomas; inflammatory disorders such as immune and non-immune inflammation; chronic articular rheumatism and psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation and wound healing; telangiectasia psoriasis scleroderma, pyogenic granuloma, cororany collaterals, ischemic limb angiogenesis, corneal diseases, rubeosis, arthritis, diabetic neovascularization, fractures, vasculogenesis, hematopoiesis.

One potential benefit of the combination of an anti-angiogenic agent and a chemotherapeutic agent may be an improvement in the treatment and control of an angiogenic dependent condition with reduced doses of a chemotherapeutic agent. The combination can be administered for a prolonged period of time, or optionally a shorter duration of treatment may be administered due to the increased effectiveness of the combination.

Depending on the nature of the combinatory therapy, administration of the polypeptide therapeutic agents of the invention may be continued while the other therapy is being administered and/or thereafter. Administration of the polypeptide therapeutic agents may be made in a single dose, or in multiple doses. In some instances, administration of the polypeptide therapeutic agents is commenced at least several days prior to the conventional therapy, while in other instances, administration is begun either immediately before or at the time of the administration of the conventional therapy.

In one embodiment, the anti-angiogenesis agent can be administered in combination with chemotherapeutic and other therapeutic agents, as well as radio-therapies. The chemotherapeutic agent may be selected from the group consisting of *vinca* alkaloid, camptothecan, taxane, or platinum analogue, including vincristine, vinblastine, vinorelbine, vindesine, paclitaxel, docetaxel, 5 FU, cisplatin, carboplatin, irinotecan, topotecan or cyclophosphamide. The chemotherapeutic agent can be administered in a low-dose regimen, in combination with the anti-angiogenic agent because of the anti-tumor effect of the anti-angiogenic agent. The chemotherapeutic agent can be administered at less than the maximum tolerated dose.

It is contemplated that the anti-angiogenic agent may be used with anti-neoplastic agents, including the following anti-neoplastic agents: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other anti-neoplastic compounds include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; atrsacrine; anagrelide; anastrozole; andrographolide; angiogenesis inhibitors; antagonist D; antagonist G; antarelix; anti-dorsalizing morphogenetic polypeptide-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocannycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance genie inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer. Those of ordinary skill in the art will recognize also numerous other compounds that fall within this category of agents that are useful in combination with the anti-angiogenic agent.

It is contemplated that the anti-angiogenic agent may be used with Anti-cancer Supplementary Potentiating Agents, including the following Supplementary Potentiating Agents: Anti-cancer Supplementary Potentiating Agents: Tricyclic anti-depressant drugs (e.g., imipramine, desipramine, amitryptyline, clomiprainine, trimipramine, doxepin, nortriptyline, protriptyline, amoxapine and maprotiline); non-tricyclic anti-depressant drugs (e.g., sertraline, trazodone and citalopram); Ca.sup.++ antagonists (e.g., verapamil, nifedipine, nitrendipine and caroverine); Calmodulin inhibitors (e.g., prenylamine, trifluoroperazine and clomipramine); Amphotericin B; Triparanol analogues (e.g., tamoxifen); antiarrhythmic drugs (e.g., quinidine); antihypertensive drugs (e.g., reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor. Those of ordinary skill in the art will recognize also numerous other compounds that fall within this category of agents that are useful in combination with the anti-angiogenic agent.

One embodiment also includes a kit for treating an angiogenic dependent condition in a mammal comprising an anti-angiogenic agent and a chemotherapeutic agent. The combination of agents is provided to allow administration in an amount and frequency therapeutically effective to produce an inhabitation or regression of angiogenesis. In certain embodiments, the anti-angiogenic agent and/or polynucleotides are administered alone or in combination with an anti-inflammatory agent. Anti-inflammatory agents that may be administered with the anti-angiogenic agents of the invention include, but are not limited to, corticosteroids (e.g. betamethasone, budesonide, cortisone, dexamethasone, hydrocortisone, methylprednisolone, prednisolone, prednisone, and triamcinolone), nonsteroidal anti-inflammatory drugs (e.g., diclofenac, diflunisal, etodolac, fenoprofen, floctafenine, flurbiprofen, ibuprofen, indomethacin, ketoprofen, meclofenamate, mefenamic acid, meloxicam, nabumetone, naproxen, oxaprozin, phenylbutazone, piroxicam, sulindac, tenoxicam, tiaprofenic acid, and tolmetin.), as well as antihistamines, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

Pharmaceutical agents include the following categories and specific examples. It is not intended that the category be limited by the specific examples. Those of ordinary skill in the art will be able to identify readily those pharmaceutical agents that have utility outside of the central nervous system. Those of ordinary skill in the art will recognize also numerous other compounds that fall within the categories and that are useful according to the invention.

In some embodiments, it may be desired to increase the solubility and blood circulation time of the ant-angiogenic agent. To increase polypeptide solubility, blood circulation time, polyethylene glycol may be used to derivatize polypeptides of the invention, include, for example, poly(ethylene glycol) (PEG), poly(vinylpyrrolidone), polyoxomers, polysorbate and poly(vinyl alcohol), with PEG polymers being particularly preferred. The PEG polymers are PEG polymers having a molecular weight from about 100 to about 40,000. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions. In one example, the anti-angiogenic agent was PEGylated with a PEG-chain of 20 kDa.

The polyethylene glycol molecules (or other chemical moieties) should be attached to the polypeptide with consideration of effects on functional or antigenic domains of the polypeptide. There are a number of attachment methods available to those skilled in the art. For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group. One may specifically desire polypeptides chemically modified at the N-terminus. Using polyethylene glycol as an illustration of the present composition, one may select from a variety of polyethylene glycol molecules (by molecular weight, branching, etc.), the proportion of polyethylene glycol molecules to polypeptide (polypeptide) molecules in the reaction mix, the type of pegylation reaction to be performed, and the method of obtaining the selected N-terminally pegylated polypeptide. Under the appropriate reaction conditions, substantially selective derivatization of the polypeptide at the N-terminus with a carbonyl group containing polymer is achieved.

A variety of administration routes are available. The particular mode selected can depend upon the anti-angiogenic agent, the particular condition being treated and the dosage required for efficacy. These methods may be practiced using any mode of administration that is medically acceptable, meaning any mode that produces effective levels of an immune response without causing clinically unacceptable adverse effects. Certain modes of administration are parenteral routes.

Certain specific embodiments also provide pharmaceutical compositions. Such compositions comprise a therapeutically effective amount of active component (e.g., the anti-angiogenic agent, the anti-angiogenic agent plus chemotherapeutic or the anti-angiogenic agent plus anti-inflammatory agent), and a pharmaceutically acceptable carrier. Such pharmaceutical carriers can be sterile liquids, such as water and oils, including those of petroleum, animal, vegetable or synthetic origin, such as peanut oil, soybean oil, mineral oil, sesame oil and the like. Water is a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Such compositions will contain a therapeutically effective amount of the anti-angiogenic agent together with a suitable amount of carrier so as to provide the form for proper administration to the patient. The formulation should suit the mode of administration.

The amount of the anti-angiogenic agent that will be effective in the treatment (see, e.g. FIG. 9), inhibition and prevention of a disease or disorder associated with aberrant expression and/or activity of a therapeutic polypeptide can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

More specifically, the agent or pharmaceutical compositions can be tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

It is contemplated that the anti-angiogenic agent can be formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter.

In a specific embodiment, it may be desirable to administer the anti-angiogenic agent locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. When administering a polypeptide, care should be taken to use materials to which the polypeptide does not absorb.

In a specific embodiment where the anti-angiogenic agent is a nucleic acid encoding a polypeptide, the nucleic acid can be administered in vivo to promote expression of its encoded polypeptide, by constructing it as part of an appropriate nucleic acid expression vector and administering it so that it becomes intracellular, e.g., by use of a retroviral vector, or by direct injection, or by use of microparticle bombardment, or coating with lipids or cell-surface receptors or transfecting agents, or by administering it in linkage to a homeobox-like peptide which is known to enter the nucleus, etc. Alternatively, a nucleic acid can be introduced intracellularly and incorporated within host cell DNA for expression, by homologous recombination.

Other embodiments are directed to vectors containing a polynucleotide encoding anti-angiogenic agent, host cells, and the production of anti-angiogenic agent by synthetic and recombinant techniques. The vector may be, for example, a phage, plasmid, viral, or retroviral vector. Retroviral vectors may be replication competent or replication defective. In the latter case, viral propagation generally will occur only in complementing host cells. The polynucleotides encoding the anti-angiogenic agent may be joined to a vector containing a selectable marker for propagation in a host. Generally, a plasmid vector is introduced in a precipitate, such as a calcium phosphate precipitate, or in a complex with a charged lipid. The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated. As indicated, the expression vectors will preferably include at least one selectable marker.

It is contemplated that regulatory genes and sequence may used with the expression and replication of the anti-angiogenic agent. The nature of the regulatory sequences for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Promoters may be constitutive or inducible. Regulatory sequences may also include enhancer sequences or upstream activator sequences, as desired.

In one embodiment, polynucleotides encoding the anti-angiogenic agent may be fused to polynucleotides encoding signal sequences which will direct the localization of a polypeptide to particular compartments of a prokaryotic or eukaryotic cell and/or direct the secretion of a polypeptide. For example, in *E. coli*, one may wish to direct the expression of the protein to the periplasmic space. Several vectors are commercially available for the construction of fusion proteins which will direct the localization of a protein.

One specific embodiment provides stents, comprising a generally tubular structure (which includes for example, spiral shapes), the surface of which is coated with an anti-angiogenic agent as described above. A stent can be a scaffolding, usually cylindrical in shape, that may be inserted into a body passageway (e.g., bile ducts) or a portion of a body passageway, which has been narrowed, irregularly contoured, obstructed, or occluded by a disease process (e.g., ingrowth by a tumor) in order to prevent closure or reclosure of the passageway.

One specific embodiment also provides use of an anti-angiogenic agent in a wide variety of surgical procedures. For example, within one aspect of the present invention an anti-angiogenic protein (in the form of, for example, a spray or film) may be utilized to coat or spray an area prior to removal of a tumor, in order to isolate normal surrounding tissues from malignant tissue, and/or to prevent the spread of disease to surrounding tissues. Within yet other aspects of the present invention, surgical meshes which have been coated with anti-angiogenic protein may be utilized in any procedure wherein a surgical mesh might be utilized.

The examples which follow are set forth to aid in understanding the invention, but are not intended to, and should not be construed as, limiting the scope of the invention in any manner.

EXAMPLES

Example 1: Expression of Anti-Angiogenic Agent

Figure 2:
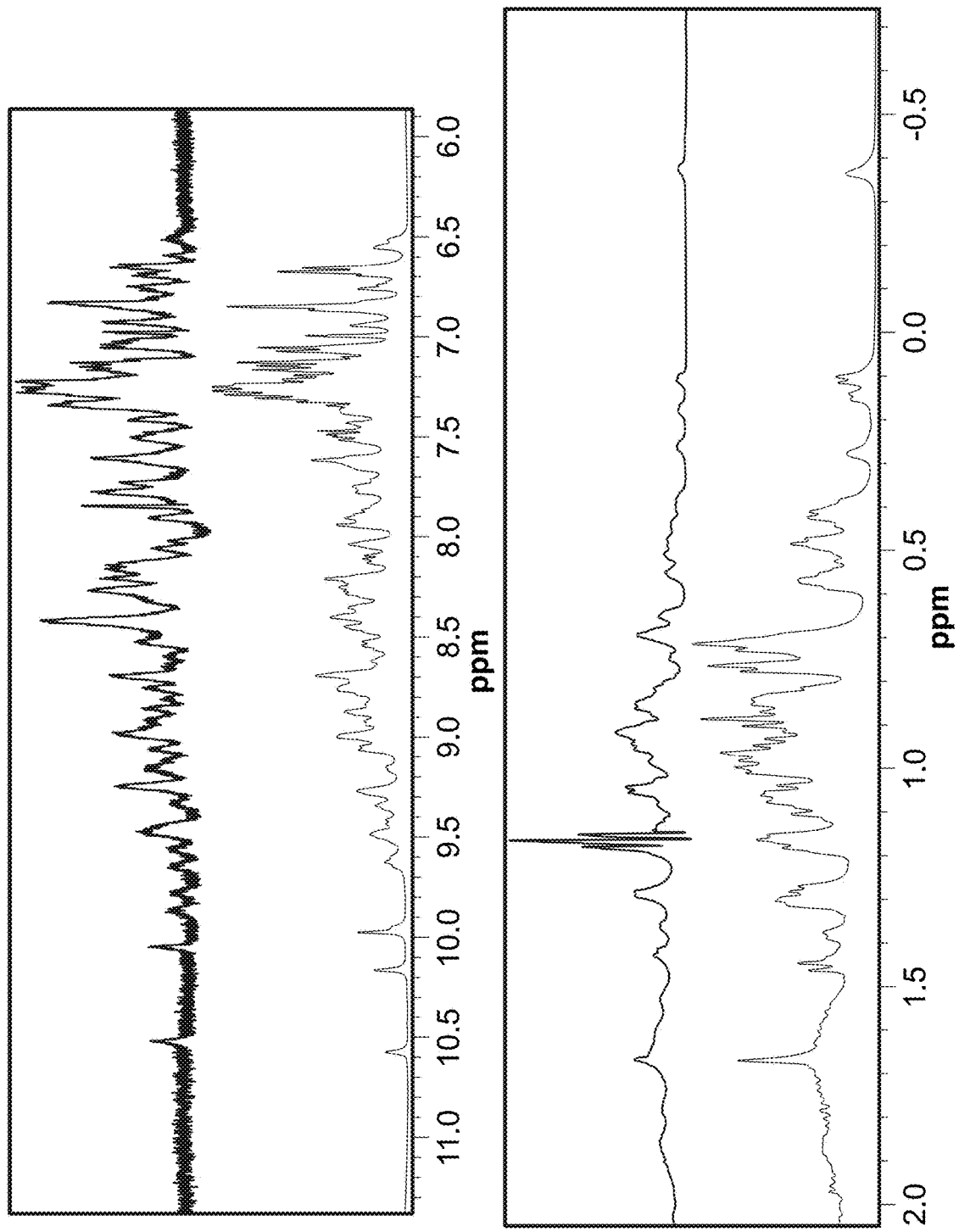
FIG. 2 shows the NMR spectrum of a folded (top) and an unfolded (bottom) anti-angiogenic agent and host protein.

The anti-angiogenic agent was expressed and purified from bacterial *E. coli*. To help ensure the designed polypeptide still folded properly, the structure was confirmed with 1H-NMR analyses. The NMR spectrum of anti-angiogenic agent (120 μM) and CD2-D1 (120 μM) were compared. As shown in FIG. 2, the NMR spectrum of the anti-angiogenic agent was almost identical to that of CD2-D1 (top), whereas the unfolded polypeptide (by organic solvent) showed a completely different spectrum (bottom). The resulting polypeptide exhibited very similar structural properties as demonstrated by similarity of $^1$H-NMR, CD, and fluorescence spectrum of both the host protein and the developed protein.

Example 2: Endothelial Cells and Apoptosis

Figure 3B:
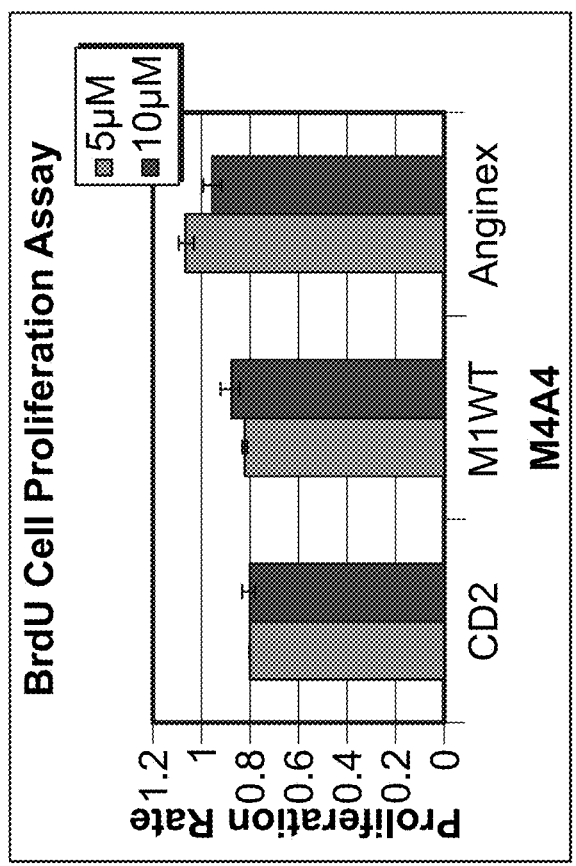
FIG. 3B shows a proliferation assay of an anti-angiogenic agent versus a prior art agent (Anginex) with M4A4 cancer cells.
Figure 3A:
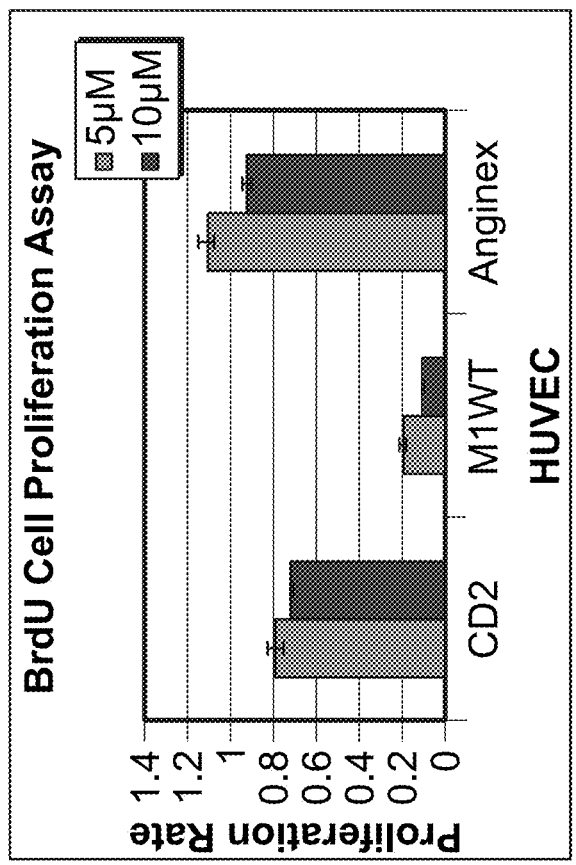
FIG. 3A shows a proliferation assay of an anti-angiogenic agent versus a prior art agent (Anginex) with HUVEC cells.
Figure 9:
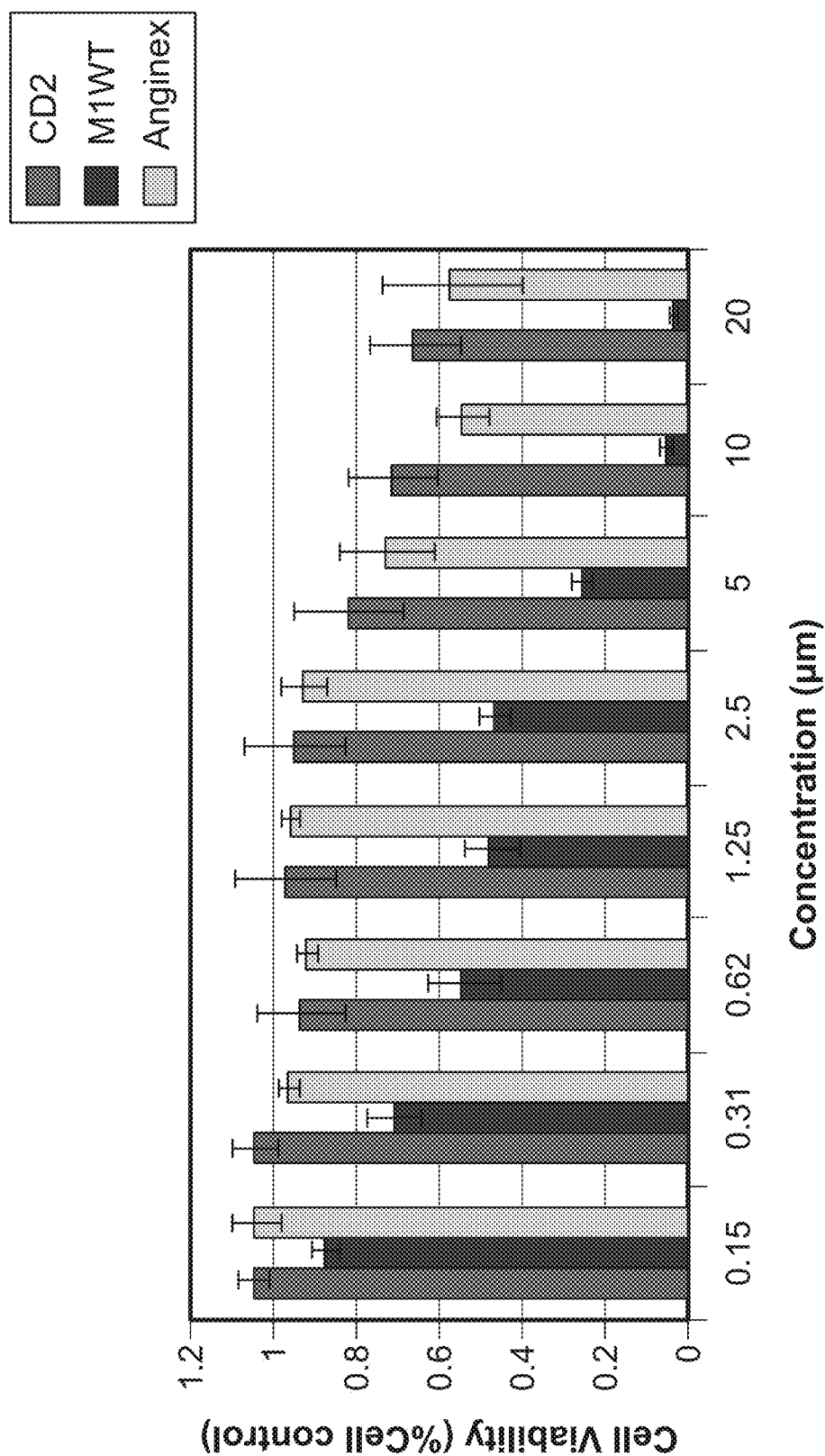
FIG. 9 shows cell viability can vary with dose.

To determine the effects of the anti-angiogenic agent on the endothelial cells, cell viability assays were carried out using HUVEC cells. The cells were treated with various concentrations of one example of a developed anti-angiogenic agent, anginex, and host polypeptide with which the anti-angiogenic agent was derived. As shown in FIG. 3A, the anti-angiogenic agent was more effective in apoptosis induction of the HUVEC cells (FIG. 2A). We further tested whether the effects were specific to endothelial cells. To this end, cell proliferation assays were carried out with HUVEC, M4A4, cells in the presence of 5 μM or 10 μM of Anti-angiogenic agent, Anginex, and host protein. As shown in FIGS. 3B and 9, it was clear that strong inhibition in cell proliferation by the agent with HUVEC cells, while no effects were observed with epithelial M4A4 cells. The observations indicated that the effects of anti-angiogenic agent were endothelial cell specific.

Example 3: Inhibition of Tumor Growth of Xenograft of PC-3 Cells

The strong activity of the anti-angiogenic agent in inhibiting growth and induction of apoptosis on HUVEC cells was evident. A xenograft model of PC-3 cells was prepared using immunodeficient mice. Tumor bearing mice (6 mice per group) were treated with an anti-angiogenic agent (10 mg/kg), a PEGylated anti-angiogenic agent (10 mg/kg), a host protein (10 mg/kg), and buffer saline for two weeks via daily dose. The treatments were started 7 days post tumor inoculation. The tumors were measured either by volume or by bioluminescence of tumor cells.

Figure 4A:
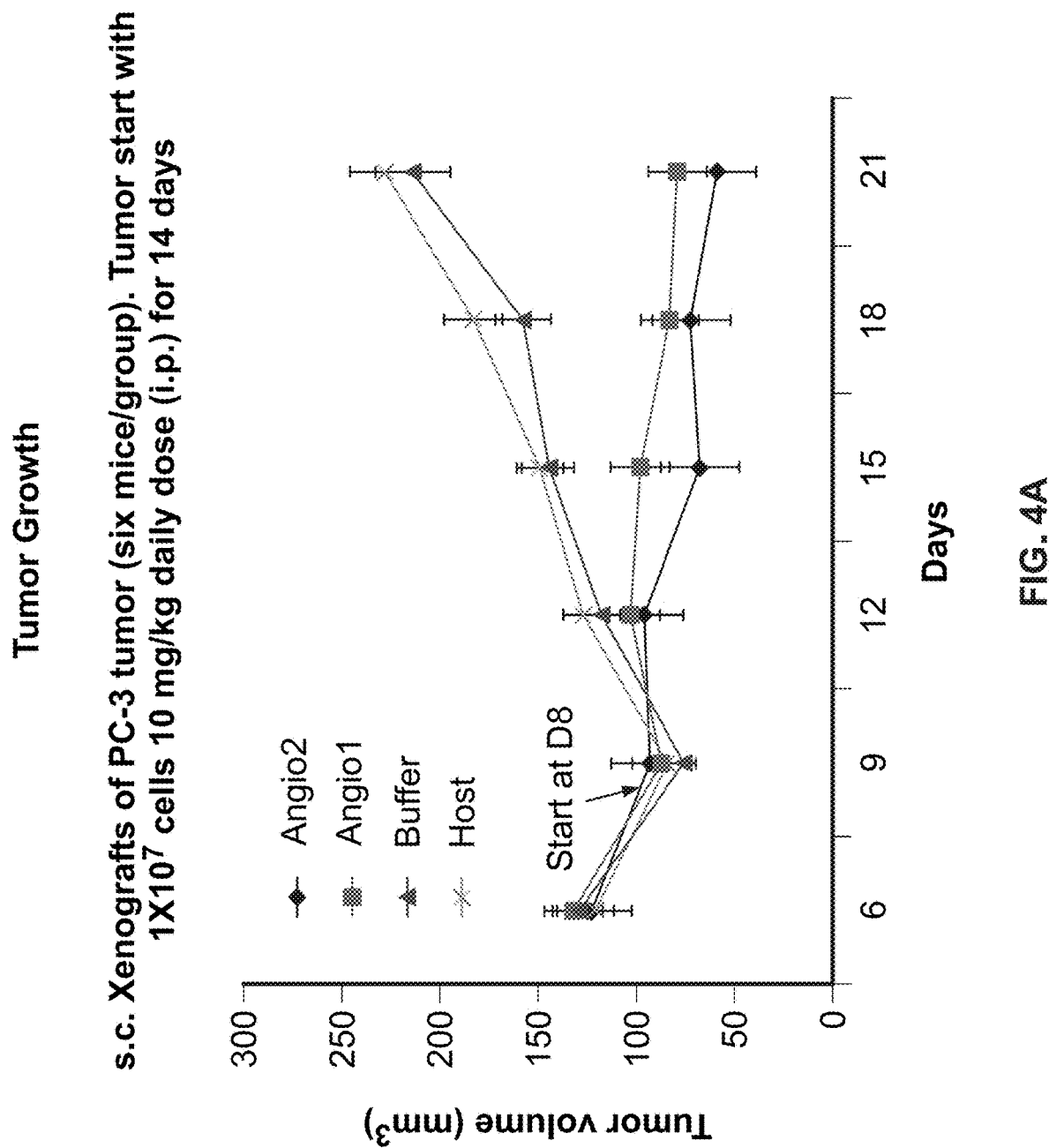
FIG. 4A shows graphically that tumor volume remained relatively constant during the course of treatment with an anti-angiogenic agent when the treatment was started after 8 days.
Figure 4B:
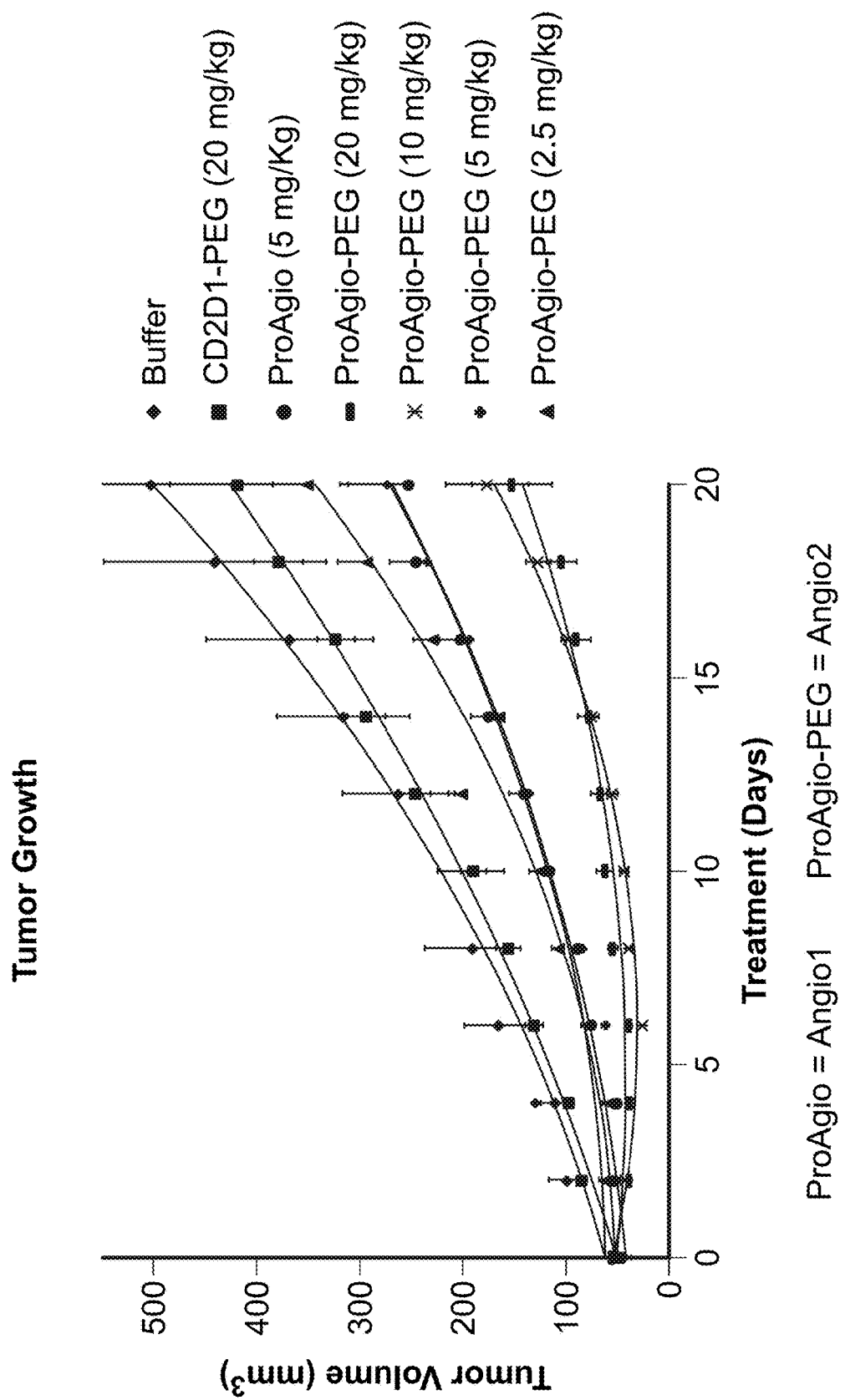
FIG. 4B shows graphically that tumor volume remained relatively constant during the course of treatment with an anti-angiogenic agent when the treatment was started after 22 days.

As shown in FIGS. 4A and 4B, the anti-angiogenic agent and the anti-angiogenic agent-PEG inhibited the tumor growth. FIG. 4A shows graphically that tumor volume remained relatively constant during the course of treatment with an anti-angiogenic agent when treatment was started after 8 days. FIG. 4B shows graphically the dose dependent effect and that tumor volume remained relatively constant during the course of treatment with an anti-angiogenic agent when treatment was started after 22 days. As controls, the tumors grew in normal rate in the mice treated with buffer and the host proteins. At the end of treatment course, tumors in each treatment group were cut out and weighed.

Figure 5:
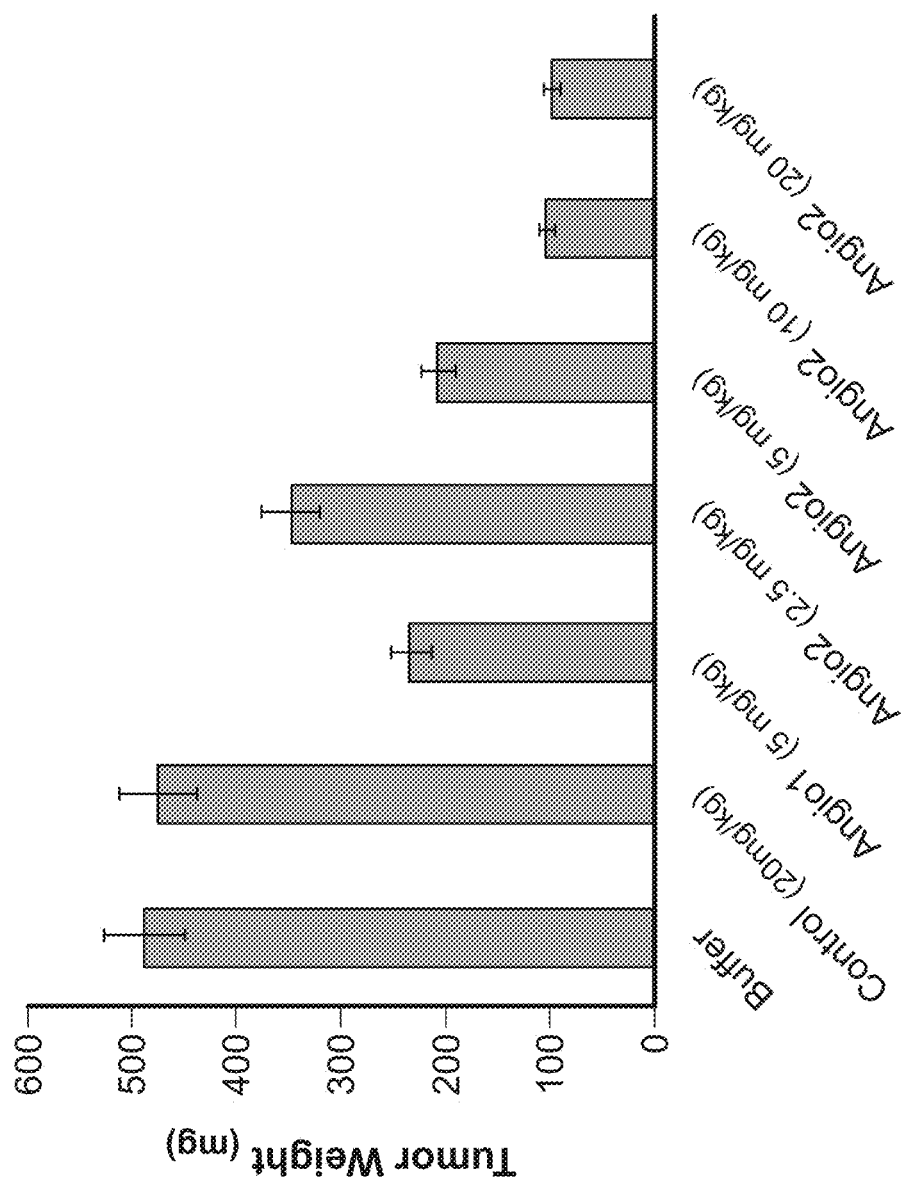
FIG. 5 shows graphically that there were substantial differences in the tumor weights by the end of the first treatment with an anti-angiogenic agent.

As shown in FIG. 5, there were substantial differences in the tumor weights comparing the anti-angiogenic agent and control groups. This time the tumors were initialized with $2 \times 10^6$ cells. The treatments were started at 22 days after tumor implantation. The anti-angiogenic agent inhibited the tumor growth completely.

Figure 6:
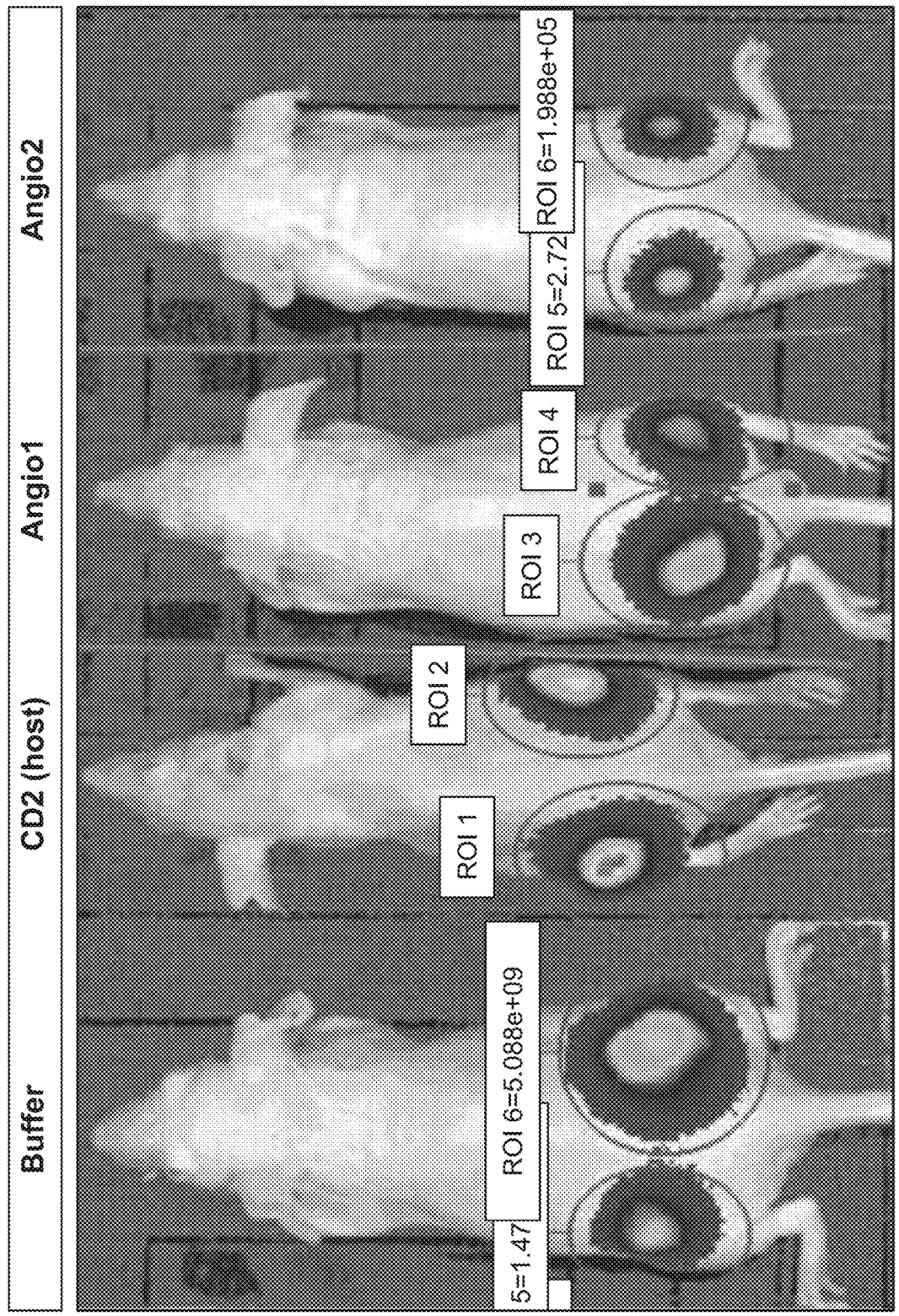
FIG. 6 shows pictorially that the tumors grew in normal rate in the mice treated with buffer and the host proteins, and substantially slower in the mice treated with the anti-angiogenic agent.

As shown in FIG. 6, in the control groups, the tumors grew at a normal rate in the mice treated with buffer and the host proteins (CD2). From the images, it can be seen that the tumors remained steady when treated with the exemplary anti-angiogenic agents. For reference purposes only, Protein M1WT may be referred to as Agio1 and M1PEG may be referred to as Agio2.

Example 4: Vessel Density after the Treatments

Figure 7:
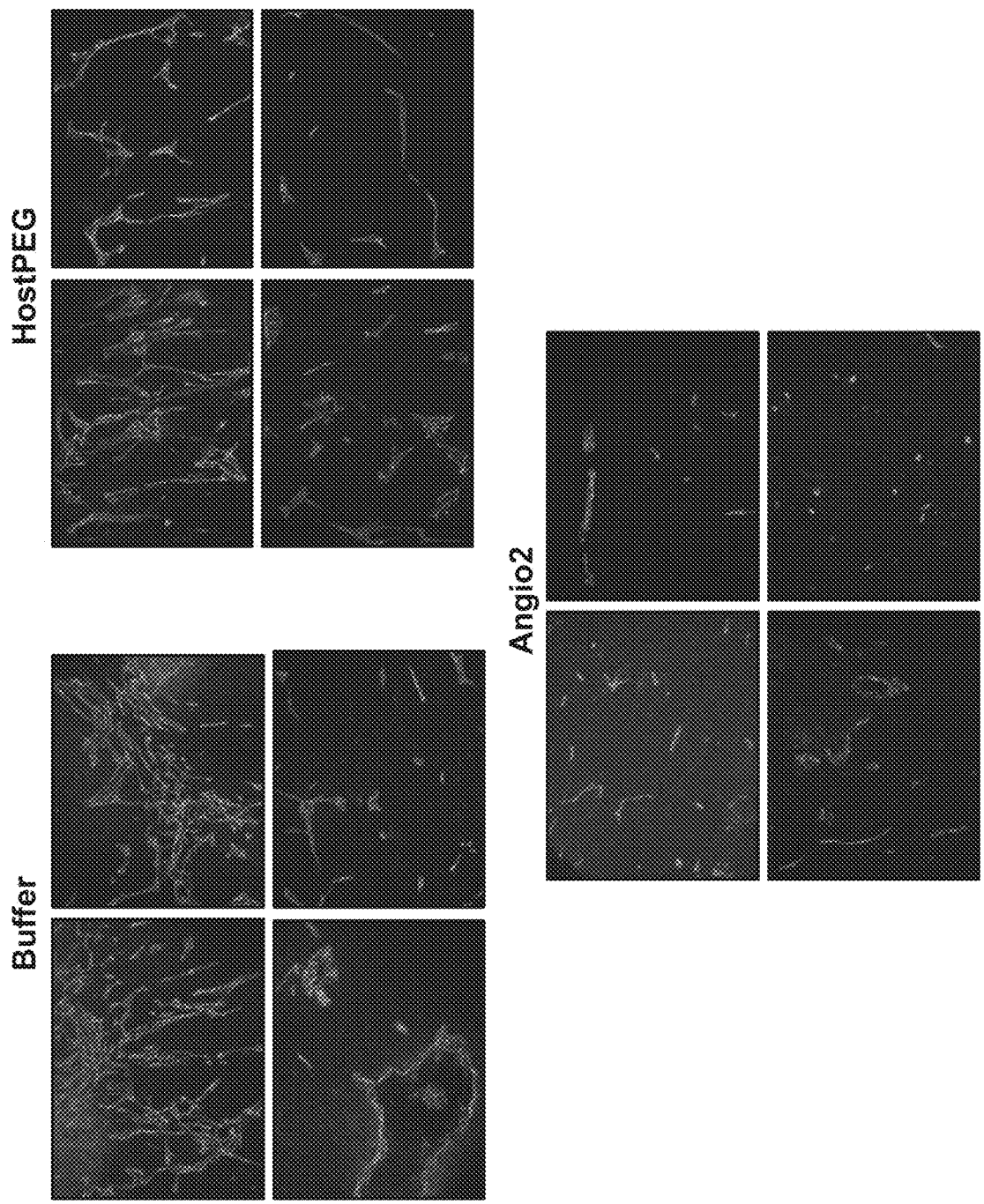
FIG. 7 shows the results of vessel density studies of mice treated with an anti-angiogenic agent.

FIG. 7 shows that the vessel density, monitored using immunofluorecense staining of tumor tissue sections collected from treated mice, was dramatically reduced after treatment with an anti-angiogenic agent with PEGylated anti-angiogenic agent compared to the group of treatment with PEGylated host protein and buffer. To determine whether the effects of the anti-angiogenic agent treatment were indeed on the tumor blood vessels, the tumors after treatments were harvested. Tissue slides were prepared from the collected tumors. The slides were immunostained with antibody against CD31, a molecular marker specific for endothelial cells. The immunostaining of the tumor tissue slides were visualized by confocal microscopy. The results indicated that the anti-angiogenic agent had specific effects on tumor angiogensis.

Example 5: Toxicity and Immunogenicity of the Anti-Angiogenic Agent

Figure 8:
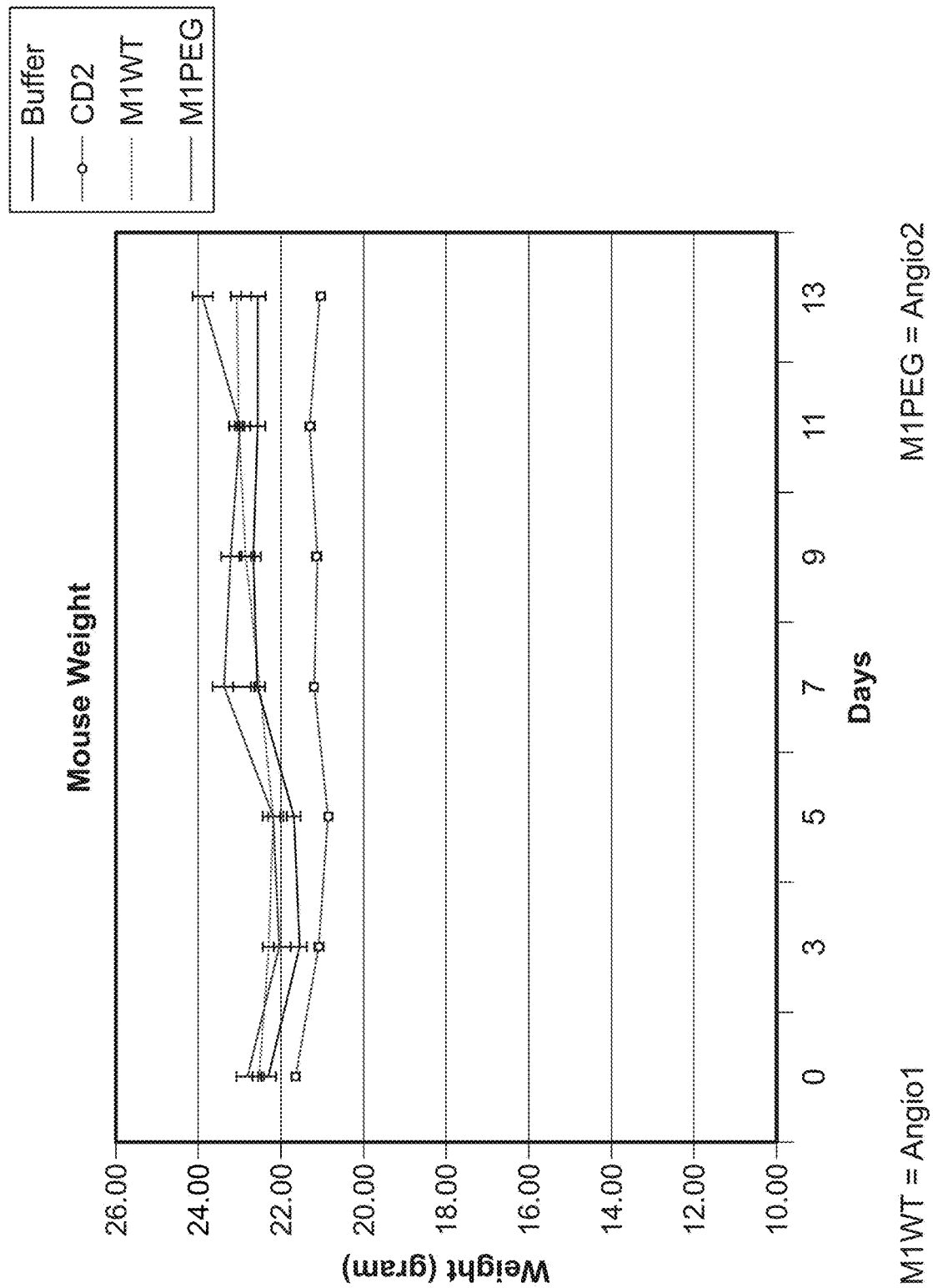
FIG. 8 shows that no significant changes in mice body mass were observed in any treatment group.

Toxicity of the parental protein of domain 1 of CD2 was previously analyzed and was not toxic in mice. To help ensure that the new designs did not alter the toxicity of the protein, the toxicity of the anti-angiogenesis polypeptide was examined using CD-1 mice. Firstly, the body weights of tumor bearing nude mice were carefully monitored during a 14-day treatment course. As shown in FIG. 8, no significant changes in mice body weight were observed in any treatment group. In addition, the toxicity was tested in normal CD-1 mice. Three groups of mice (7 mice per group) were injected i.v. with one dose, two doses and three doses of 100 µl of the polypeptide (100 mg/kg, 20 times of used dosage) with three day intervals between each injection. The animals were returned to their cages for 30 days. No deaths were observed among the tested mice. All animals behaved normally (no change in eating habits; no abnormal weight gain or loss; and no abnormal appearance on fur).

The toxicity studies showed that the anti-angiogenic agent and anti-angiogenic agent with PEG did not have acute toxicity for at least three doses that were approximately 20 fold higher than the dosage used in the tumor mice treatment. In addition, we also tested whether there were any liver, kidney, and cardiovascular damages upon treatment with the anti-angiogenic agent and anti-angiogenic agent with PEG. Histological analyses revealed no damage to organs of treated animals.

Example 6: N-Linked Glycosylation

The polypeptide shown in Sequence ID No: 11 was expressed and purified from the *Pichia pastoris* expression system. Expression of this polypeptide in yeast *Pichia pastoris* was achieved by both intracellular and secretion expression. This polypeptide was further purified using an ion exchange column. The polypeptide was expressed as a His-tag polypeptide. The His-tag was removed by thrombin cleavage. The glycosylated protein expressed and purified from Yeast *Pichia pastoris* was an anti-angiogenic agent and was found have N-linked glycosylation. As shown in FIG. 13, cells treated by various examples of the anti-angiogenic agent showed robust viability.

Example 7: Sequences

SEQ ID NO:1 is the amino acid sequence of domain one of CD2 from a rat (WT Rat CD2-D1):

```
RDSGTVWGAL GHGINLNIPN FQMTDDIDEV RWERGSTLVA

EFKRKMKPFL KSGAFEILAN GDLKIKNLTR DDSGTYNVTV

YSTNGTRILN KALDLRILE
```

SEQ ID NO:2 is the amino acid sequence of domain one of CD2 from human (WT Human CD2-D1):

```
KEITNALETWGALGQDINLDIPSFQMSDDIDDIKWEKTSDKKKIAQFRK

EKETFKEKDTYKLFKNGTLKIKHLKTDDQDIYKVSIYDTKGKNVLEKIF

DLKIQER
```

SEQ ID NO:3, referred to as M1WT or Agio1, is the amino acid sequence of a variant domain one of CD2 derived from SEQ ID NO1 by mutations W7Q, G8M, A9K, D94N, R96K, I97V, L98I, and E99I:

```
RDSGTVQMKL GHGINLNIPN FQMTDDIDEV RWERGSTLVA

EFKRKMKPFL KSGAFEILAN GDLKIKNLTR DDSGTYNVTV

YSTNGTRILN KALNLKVII
```

SEQ ID NO:4 is the amino acid sequence of a variant domain one of CD2 d derived from SEQ ID NO1 by mutations E41I, K43V, K45L, M46G, K47S, P48V, and G53L:

```
RDSGTVKWKA GHGINLNIPN FQMTDDIDEV RWERGSTLVA

EFKRKMKPFL KSGAFEILAN GDLKIKNLTR DDSGTYNVTV

YSTNGTRILN KALSLDVNI
```

SEQ ID NO:5 is the amino acid sequence of a variant domain one of CD2 derived from SEQ ID NO1 by mutations E41N, M46Q, and F49S:

```
RDSGTEVIKA GHGINLNIPN FQMTDDIDEV RWERGSTLVA

EFKRKMKPFL KSGAFEILAN GDLKIKNLTR DDSGTYNVTV

YSTNGTRILN KALKLTAIL
```

SEQ ID NO:6, referred to as ProAgio-PEG or Agio2, is the amino acid sequence of a variant domain one of CD2 derived from SEQ ID NO3 by mutations M23C:

```
RDSGTVQMKL GHGINLNIPN FQCTDDIDEV RWERGSTLVA

EFKRKMKPFL KSGAFEILAN GDLKIKNLTR DDSGTYNVTV

YSTNGTRILN KALNLKVII
```

SEQ ID NO:7 is the amino acid sequence of a variant domain one of CD2 derived from SEQ ID NO1 by mutations E41I, K43V, K45L, M46G, K47S, and F49S:

RDSGTVWGAL GHGINLNIPN FQMTDDIDEV RWERGSTLVA

IFVRLGSVKM KPLLKSGAFE ILANGDLKIK NLTRDDSGTY

NVTVYSTNGT RILNKALDLR ILE

SEQ ID NO:8 is the amino acid sequence of a variant domain one of CD2:

RDSGTVWGALGHGINLNIPNFQMTDDIDEVRWERGSTLVANFKRKQKPS

LKSGAFEILANGDLKIKNLTRDDSGTYNVTVYSTNGTRILNKALDLRIL

E

SEQ ID NO:9, referred to as hProAngioB or Angio3, is the amino acid sequence of a variant domain one of CD2 derived from SEQ ID NO:2 by mutations E8S, T9V, W10Q, G11M, A12K, K61E, F63L, T67A, Y86A, D99N, I102V, Q103I, E104I and deletion of R105:

KEITNALSVQMKLGQDINLDIPSFQMSDDIDDIKWEKTSDKKKIAQFRK

EKETFKEKDTYELLKNGALKIKHLKTDDQDIYKVSIADTKGKNVLEKIF

NLKVIIR

SEQ ID NO:10, referred to as hProAgio or Agio4, is the amino acid sequence of a variant domain one of CD2 derived from SEQ ID NO:9 by mutations M30C:

KEITNALSVQMKLGQDINLDIPSFQCSDDIDDIKWEKTSDKKKIAQFRK

EKETFKEKDTYELLKNGALKIKHLKTDDQDIYKVSIADTKGKNVLEKIF

NLKVII

SEQ ID NO:11, referred to as hProAgioY or Agio5, is the amino acid sequence of a variant domain one of CD2 form yeast:

KEITNALSVQMKLGQDINLDIPSFQMSDDIDDIKWEKTSDKKKIAQFRK

EKETFKEKDTYKLFKNGTLKIKHLKTDDQDIYKVSIADTKGKNVLEKIF

NLKVII

SEQ ID NO: 12, referred to as Agio6, is the amino acid sequence of a variant domain one of CD2 derived from SEQ ID NO:9 by mutations M30C and the addition of a terminal glycine (G):

GKEITNALSVQMKLGQDINLDIPSFQCSDDIDDIKWEKTSDKKKIAQFR

KEKETFKEKDTYELLKNGALKIKHLKTDDQDIYKVSIADTKGKNVLEKI

FNLKVII

Example 7: Tumor Growth Suppression

Figure 10:
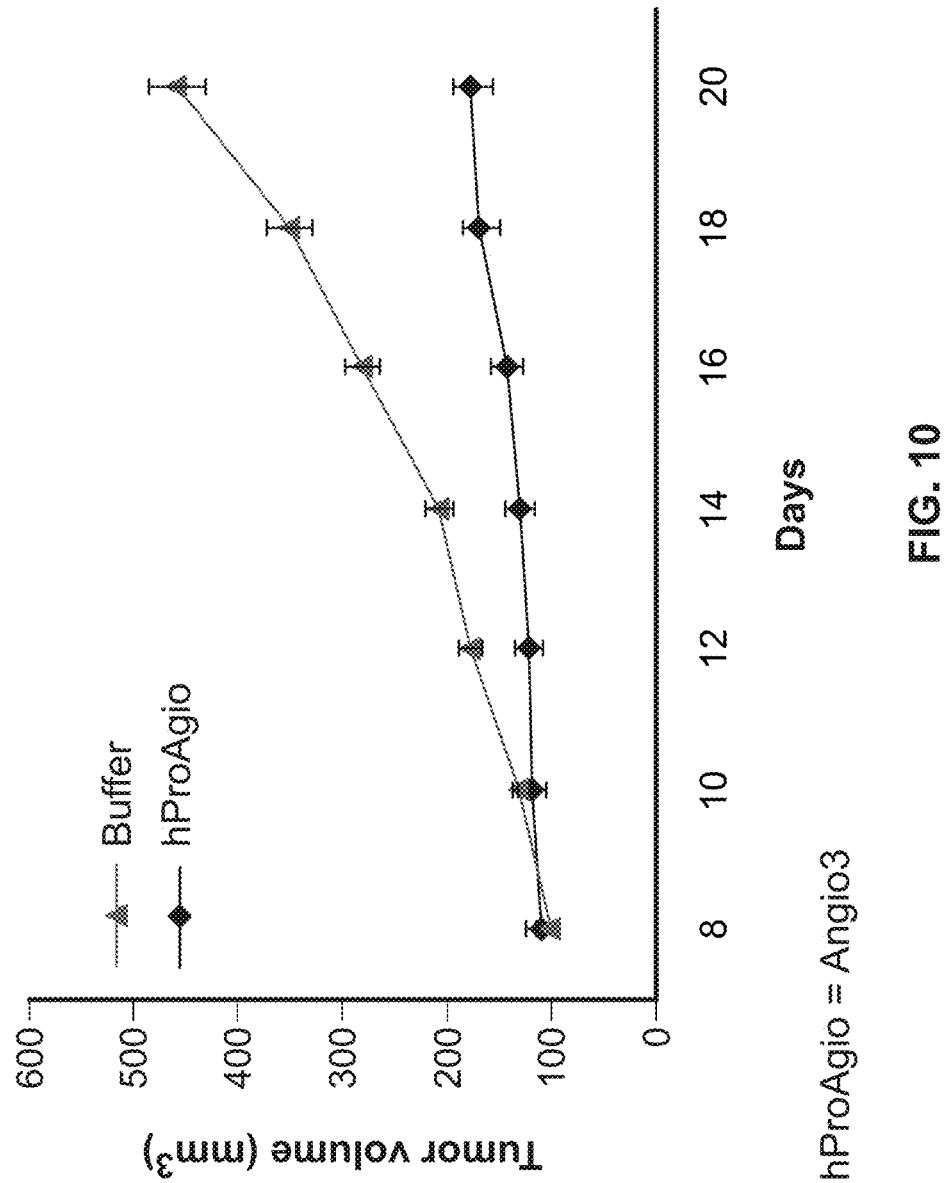
FIG. 10 shows the growth curve of the tumor through 14 days or more of treatment using different doses of the anti-angiogenic agent.

FIG. 10 shows the growth curve of the tumor through 14 days or more of treatment. The results show that hProAgio or Agio4, developed from the polypeptide encoding SEQ ID NO: 10, was effective in suppressing tumor growth. The experiments were carried out using PC-3 xenograft using hProAgio or Agio4 (10 mg/kg, daily dose) and using buffered saline as a control. The treatments were started 8 days post tumor inoculation.

Example 8: Effectiveness Against AVASTIN®

Figure 11:
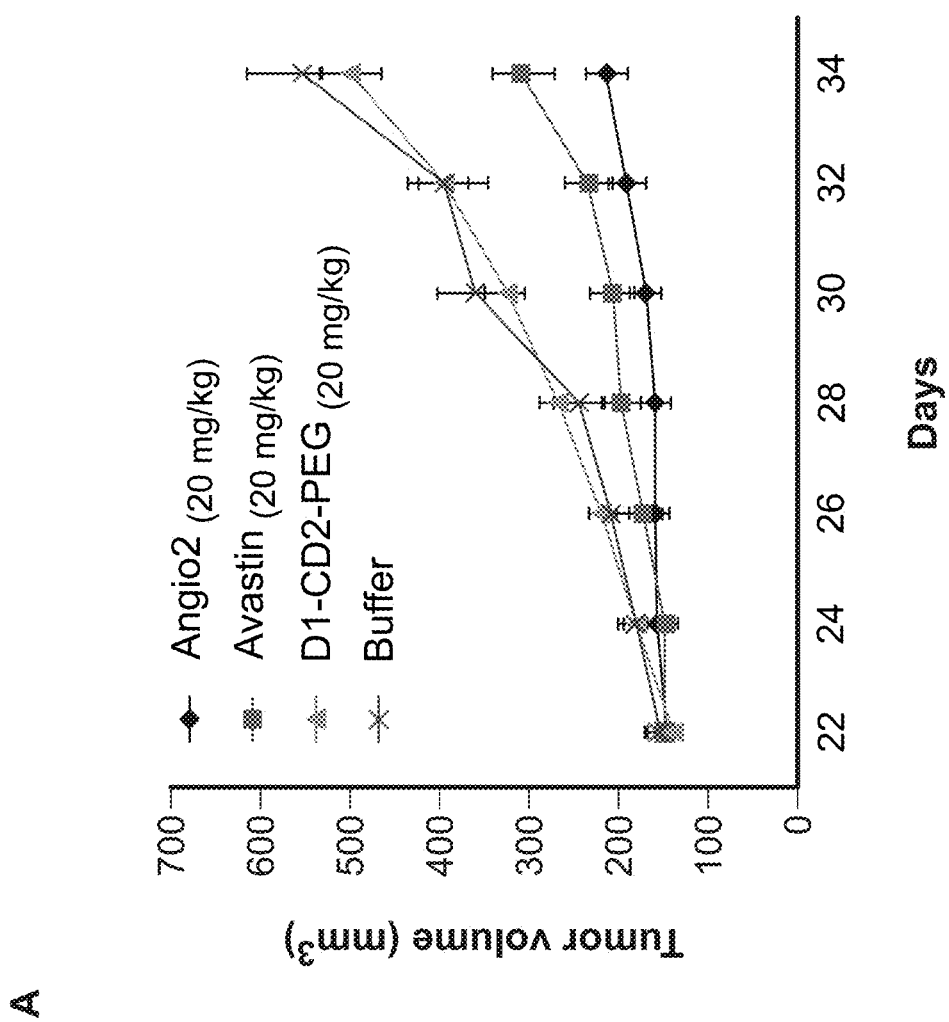
FIG. 11 is the tumor growth curve of AVASTIN® and rProAgio-PEG.
Figure 12:
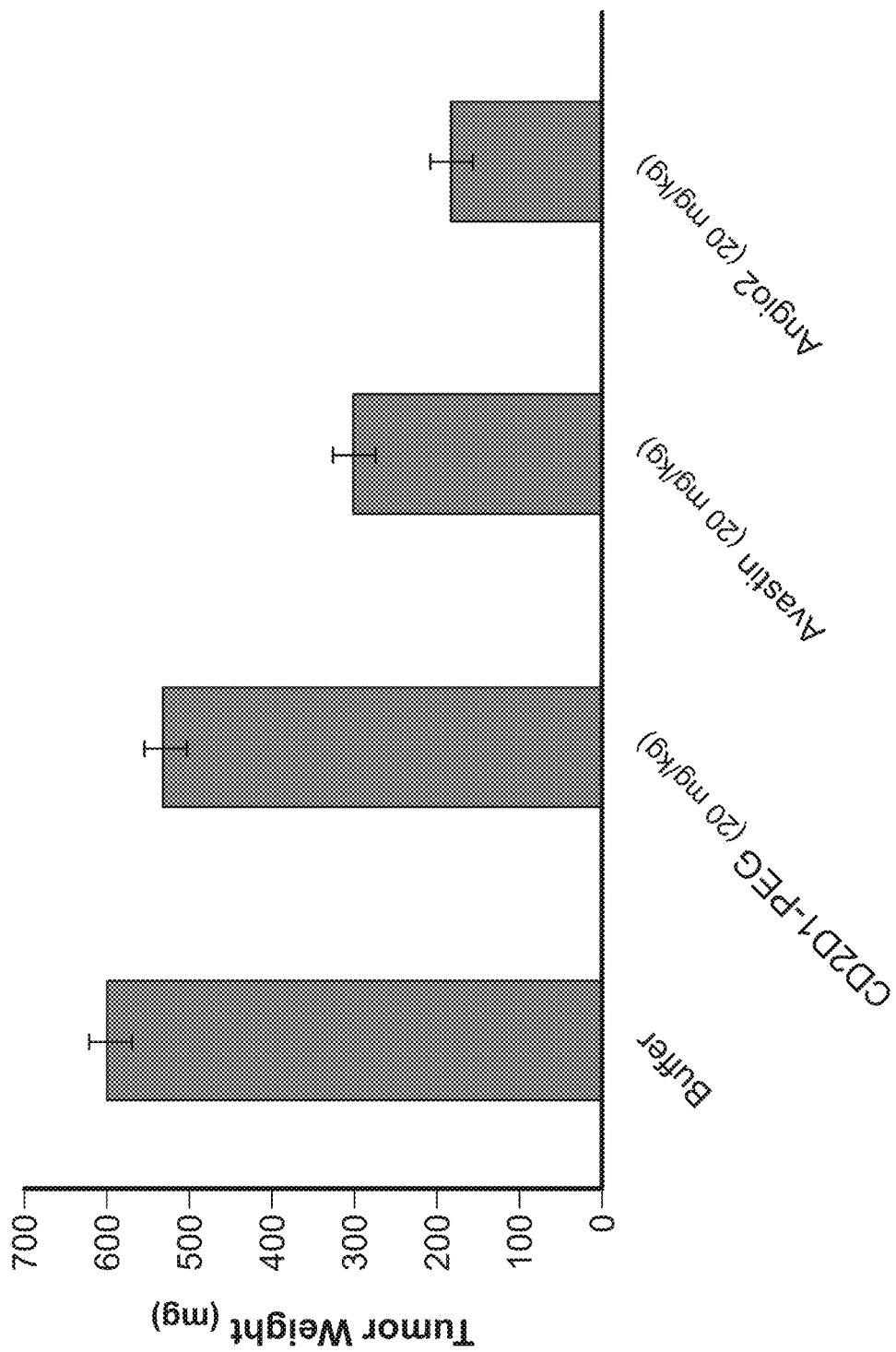
FIG. 12 shows a graphic representation of the weight of the tumor at end of 14 day treatment course.

To further test the effectiveness of the anti-angiogenic polypeptide, experiments with PC-3 xenografts using rProAgio-PEG or Agio2 (20 mg/k, daily dose) and Avastin (20 mg/kg, one dose every two days) were carried and analyzed. The treatments were started 21 days post tumor inoculation. FIG. 11 is the tumor growth curve of Avastin® and rProAgio-PEG or Agio2. FIG. 12 shows graphic representation of the weight of the tumor at end of 14 day treatment course—the tumors in each treatment group were extracted and weighed. There were significant differences in the tumor weights and growth of the animal groups that were treated by Agio2 and AVASTIN®.

The foregoing detailed description and the appended figures have been presented only for illustrative and descriptive purposes. They are not intended to be exhaustive and are not intended to limit the spirit of the invention. The embodiments were selected and described to best explain the principles of the invention and its practical applications. One skilled in the art will recognize that many variations can be made to the invention disclosed in this specification without departing from the scope and spirit of the invention.

What is claimed:

1. A polypeptide for reducing or inhibiting angiogenesis comprising an amino acid segment having a variation of domain one of cluster of differentiation 2 (CD2) protein from human or rat, wherein the polypeptide comprises the amino acid sequence according to SEQ ID NO: 12.

2. The polypeptide as claimed in claim 1, further comprising a polyethylene glycol (PEG) moiety.

3. The polypeptide as claimed in claim 1, further comprising a glycan moiety.

4. A pharmaceutical composition comprising a therapeutically effective amount of the polypeptide according to claim 1.

5. The pharmaceutical composition as claimed in claim 4, wherein the composition is in a form for systemic administration.

6. The pharmaceutical composition as claimed in claim 4, wherein the composition is an injectable solution or suspension.

7. The pharmaceutical composition as claimed in claim 4, further comprising a pharmaceutically acceptable excipient, carrier, or diluent.

8. A method of reducing angiogenesis in an individual in need thereof, the method comprising: administering to the individual a therapeutically effective dose of the polypeptide as claimed in claim 1.

9. The method as claimed in claim 8, wherein the individual has a disorder selected from the group consisting of tumor growth, atherosclerosis, diabetic retinopathy, age-related maculopathy, and retrolental fibroplasia.

10. The method as claimed in claim 8, wherein the polypeptide is administered by a route selected from the group consisting of intravenous, in or around a solid tumor, systemic, intraarterial, intraocular, intraperitoneal, and topical.

11. The method as claimed in claim 8, further comprising administering to the individual a therapeutically effective amount of a second therapeutic agent.

12. The method as claimed in claim 8, further comprising radiation therapy on the individual and administering a therapeutically effective or prophylactic amount of a second agent.

13. The method as claimed in claim 8, wherein the polypeptide is administered in the form of a pharmaceutical composition further comprising a pharmaceutically acceptable carrier or diluent.

14. The method as claimed in claim 8, further comprising administering radiation therapy to the individual.

15. The method as claimed in claim 8, wherein the angiogenesis is pathogenic.

16. The method as claimed in claim 8, wherein the individual has cancer.

17. The method as claimed in claim 16, wherein the cancer is breast carcinoma, lung carcinoma, colon carcinoma, prostate carcinoma, ovarian carcinoma, neuroblastoma, central nervous system tumor, glioblastoma multiforme, or melanoma.

* * * * *

SEQUENCE LISTING

```
Sequence total quantity: 12
SEQ ID NO: 1           moltype = AA  length = 99
FEATURE                Location/Qualifiers
source                 1..99
                       mol_type = protein
                       organism = synthetic construct
SEQUENCE: 1
RDSGTVWGAL GHGINLNIPN FQMTDDIDEV RWERGSTLVA EFKRKMKPFL KSGAFEILAN   60
GDLKIKNLTR DDSGTYNVTV YSTNGTRILN KALDRILE                          99

SEQ ID NO: 2           moltype = AA  length = 105
FEATURE                Location/Qualifiers
source                 1..105
                       mol_type = protein
                       organism = synthetic construct
SEQUENCE: 2
KEITNALETW GALGQDINLD IPSFQMSDDI DDIKWEKTSD KKKIAQFRKE KETFKEKDTY   60
```

```
KLFKNGTLKI KHLKTDDQDI YKVSIYDTKG KNVLEKIFDL KIQER          105

SEQ ID NO: 3             moltype = AA   length = 99
FEATURE                  Location/Qualifiers
source                   1..99
                         mol_type = protein
                         organism = synthetic construct
SEQUENCE: 3
RDSGTVQMKL GHGINLNIPN FQMTDDIDEV RWERGSTLVA EFKRKMKPFL KSGAFEILAN    60
GDLKIKNLTR DDSGTYNVTV YSTNGTRILN KALNLKVII                          99

SEQ ID NO: 4             moltype = AA   length = 99
FEATURE                  Location/Qualifiers
source                   1..99
                         mol_type = protein
                         organism = synthetic construct
SEQUENCE: 4
RDSGTVKWKA GHGINLNIPN FQMTDDIDEV RWERGSTLVA EFKRKMKPFL KSGAFEILAN    60
GDLKIKNLTR DDSGTYNVTV YSTNGTRILN KALSLDVNI                          99

SEQ ID NO: 5             moltype = AA   length = 99
FEATURE                  Location/Qualifiers
source                   1..99
                         mol_type = protein
                         organism = synthetic construct
SEQUENCE: 5
RDSGTEVIKA GHGINLNIPN FQMTDDIDEV RWERGSTLVA EFKRKMKPFL KSGAFEILAN    60
GDLKIKNLTR DDSGTYNVTV YSTNGTRILN KALKLTAIL                          99

SEQ ID NO: 6             moltype = AA   length = 99
FEATURE                  Location/Qualifiers
source                   1..99
                         mol_type = protein
                         organism = synthetic construct
SEQUENCE: 6
RDSGTVQMKL GHGINLNIPN FQCTDDIDEV RWERGSTLVA EFKRKMKPFL KSGAFEILAN    60
GDLKIKNLTR DDSGTYNVTV YSTNGTRILN KALNLKVII                          99

SEQ ID NO: 7             moltype = AA   length = 103
FEATURE                  Location/Qualifiers
source                   1..103
                         mol_type = protein
                         organism = synthetic construct
SEQUENCE: 7
RDSGTVWGAL GHGINLNIPN FQMTDDIDEV RWERGSTLVA IFVRLGSVKM KPLLKSGAFE    60
ILANGDLKIK NLTRDDSGTY NVTVYSTNGT RILNKALDLR ILE                     103

SEQ ID NO: 8             moltype = AA   length = 99
FEATURE                  Location/Qualifiers
source                   1..99
                         mol_type = protein
                         organism = synthetic construct
SEQUENCE: 8
RDSGTVWGAL GHGINLNIPN FQMTDDIDEV RWERGSTLVA NFKRKQKPSL KSGAFEILAN    60
GDLKIKNLTR DDSGTYNVTV YSTNGTRILN KALDLRILE                          99

SEQ ID NO: 9             moltype = AA   length = 104
FEATURE                  Location/Qualifiers
source                   1..104
                         mol_type = protein
                         organism = synthetic construct
SEQUENCE: 9
KEITNALSVQ MKLGQDINLD IPSFQMSDDI DDIKWEKTSD KKKIAQFRKE KETFKEKDTY    60
ELLKNGALKI KHLKTDDQDI YKVSIADTKG KNVLEKIFNL KVII                    104

SEQ ID NO: 10            moltype = AA   length = 104
FEATURE                  Location/Qualifiers
source                   1..104
                         mol_type = protein
                         organism = synthetic construct
SEQUENCE: 10
KEITNALSVQ MKLGQDINLD IPSFQCSDDI DDIKWEKTSD KKKIAQFRKE KETFKEKDTY    60
ELLKNGALKI KHLKTDDQDI YKVSIADTKG KNVLEKIFNL KVII                    104

SEQ ID NO: 11            moltype = AA   length = 104
FEATURE                  Location/Qualifiers
source                   1..104
                         mol_type = protein
                         organism = synthetic construct
```

-continued

```
SEQUENCE: 11
KEITNALSVQ MKLGQDINLD IPSFQMSDDI DDIKWEKTSD KKKIAQFRKE KETFKEKDTY  60
KLFKNGTLKI KHLKTDDQDI YKVSIADTKG KNVLEKIFNL KVII                  104

SEQ ID NO: 12           moltype = AA  length = 105
FEATURE                 Location/Qualifiers
source                  1..105
                        mol_type = protein
                        organism = synthetic construct
SEQUENCE: 12
GKEITNALSV QMKLGQDINL DIPSFQCSDD IDDIKWEKTS DKKKIAQFRK EKETFKEKDT  60
YELLKNGALK IKHLKTDDQD IYKVSIADTK GKNVLEKIFN LKVII                 105
```